United States Patent [19]

Onodera, deceased et al.

[11] Patent Number: 5,032,561

[45] Date of Patent: Jul. 16, 1991

[54] CATALYST COMPOSITION FOR CRACKING NON-AROMATIC HYDROCARBONS AND ISOMERIZING C8-AROMATIC HYDROCARBONS

[75] Inventors: Tamio Onodera, deceased, late of Tokuyama; by Mieko Onodera, legal representative; by Shiyou Onodera, legal representative; by Toru Onodera, legal representative, all of Tokuyama, Japan

[73] Assignee: Teijin Petrochemical Industries, Ltd., Tokyo, Japan

[21] Appl. No.: 413,721

[22] Filed: Sep. 28, 1989

[30] Foreign Application Priority Data

Sep. 29, 1988 [JP] Japan ............................... 63-242560

[51] Int. Cl.[5] ......................... B01J 29/06; B01J 29/32

[52] U.S. Cl. ........................................ 502/66; 502/71; 502/74; 502/77

[58] Field of Search ........................ 502/66, 71, 74, 77

[56] References Cited

U.S. PATENT DOCUMENTS

| | | | |
|---|---|---|---|
| 4,485,185 | 11/1984 | Onodera et al. | 502/71 |
| 4,547,618 | 10/1985 | Furbas | 502/71 |
| 4,868,145 | 9/1989 | Dessau et al. | 502/66 |

FOREIGN PATENT DOCUMENTS

| | | |
|---|---|---|
| 0018498 | 11/1980 | European Pat. Off. . |
| 0087906 | 9/1983 | European Pat. Off. . |
| 2848849 | 5/1980 | Fed. Rep. of Germany . |

*Primary Examiner*—Carl F. Dees
*Attorney, Agent, or Firm*—Sherman and Shalloway

[57] ABSTRACT

A catalyst composition consisting essentially of (a) a crystalline aluminosilicate zeolite having a silica/alumina mole ratio of at least 10 (component A) in which at least 50% of its cationic sites are occupied by alkaline earth metal cations, (b) a refractory inorganic oxide having platinum and tin supported thereon (component B) and (c) indium (component C), the indium being supported on the zeolite in component A and/or the refractory inorganic oxide in component (B). A process for decomposing non-aromatic hydrocarbons in the presence of the catalyst composition, and a process for isomerizing $C_8$-aromatic hydrocarbon, particularly xylenes, in the presence of the catalyst composition.

14 Claims, No Drawings

CATALYST COMPOSITION FOR CRACKING NON-AROMATIC HYDROCARBONS AND ISOMERIZING C8-AROMATIC HYDROCARBONS

BACKGROUND OF THE INVENTION

1. Field of the Invention

This invention relates to a catalyst composition and its use. Specifically, it relates to a catalyst composition comprising a crystalline aluminosilicate zeolite and specific metals, and its use in the cracking of non-aromatic hydrocarbons and to the isomerization of $C_8$-aromatic hydrocarbons.

More specifically, the present invention relates to an industrially advantageous catalyst composition which, when used in a process for isomerizing $C_8$-aromatic hydrocarbons which comprises isomerizing a hydrocarbon feed stock containing a $C_8$-aromatic hydrocarbon mixture which has not reached its thermodynamic equilibrium composition and small amounts of non-aromatic hydrocarbons, separating a specific xylene isomer, preferably p-xylene, from the resulting isomerization reaction mixture and recycling the remaining hydrocarbon mixture to the isomerization reaction, causes the $C_8$-aromatic hydrocarbon mixture in the hydrocarbon feed stock to reach the thermodynamic equilibrium composition, makes it possible to convert the non-aromatic hydrocarbons, which build up in the process and reduce the efficiency of the isomerization reaction, into components that can be easily removed out of the process, ensures a very little loss of the $C_8$-aromatic hydrocarbons, particularly xylenes, and decreases very little in activity after continuous operation over a long period of time, the invention also pertains to its uses.

2. Description of the Prior Art

There has been an increasing demand for xylene, particularly p-xylene, in proportion to the increase of the demand for polyester fibers and films. A typical process for producing p-xylene comprises a step of separating p-xylene from a $C_8$-aromatic hydrocarbon mixture by a crystallization method or an adsorption method, a step of bringing the remaining hydrocarbon mixture into contact with a catalyst for isomerizing m-xylene and/or o-xylene to p-xylene to convert the xylenes in the remaining hydrocarbon mixture to a xylene isomeric mixture having a composition close to the thermodynamic equilibrium composition, and a step of recycling the isomeric mixture to the p-xylene separating step.

In the above process for producing p-xylene, it is required to bring the composition of the xylene isomeric mixture in the isomerization reaction mixture to the thermodynamic equilibrium composition as close as possible, inhibit side reactions which cause a loss of xylenes, such as disproportionation reaction and hydrogenating cracking reaction, and to convert ethylbenzene, which because of its boiling point close to the boiling point of the xylenes, is difficult to separate by an ordinary distillation operation, into a higher or lower boiling component easily separable by distillation. Industrially, it is very important to satisfy these requirements in order to increase the efficiency of the isomerization reaction and reduce the cost of the p-xylene production process.

On the other hand, the $C_8$aromatic hydrocarbon mixtures heretofore used as materials for isomerization of xylenes are industrially produced by solvent extraction of catalytically reformed oils and thermally cracked in accordance with, for example, the sulfolane method, UDEX method or arosolvan method, and distilling the separated extract. The composition of the $C_8$aromatic hydrocarbon mixtures obtained by this method typically consists of 5 to 20% by weight of ethylbenzene, 15 to 25% by weight of p-xylene, 30 to 60% by weight of m-xylene and 15 to 25% by weight of o-xylene.

However, since the above method of producing the $C_8$aromatic hydrocarbon mixtures includes the solvent extraction step, the cost of the resulting hydrocarbon mixtures becomes high because extra equipment and energy are required.

In recent years, various attempts have been made to increase the yield of aromatic hydrocarbons such as benzene, toluene and xylene in the reforming of petroleum naphtha. In particular, as a result of improving a catalyst that induces dehydrogenating cyclization of paraffinic hydrocarbons, it became possible to carry out the dehydrogenating cylization under mild conditions at lower pressures. This resulted in an aromatic hydrocarbon mixture with a small content of non-aromatic hydrocarbons.

With this technical background, a method was suggested by which a $C_8$-aromatic hydrocarbon mixture having such a relatively small amount of non-aromatic hydrocarons as to make it usable as a starting material for xylene isomerization is obtained from a naphtha reformed oil by distillation treatment alone without using the solvent extraction step (Japanese Patent Publication No. 47231/1982). There was also proposed a process for producing a $C_8$-aromatic hydrocarbon mixture having a relatively low content of non-aromatic hydrocarbons, which comprises distilling a naphtha reformed oil, polymerizing olefins therein which are difficult to remove by distillation treatment alone and become a poison on the xylene isomerization reaction catalyst, and again distilling the residue (Japanese Laid-Open Patent Publication No. 181036/1985). The amount of non-aromatic hydrocarbons in the resulting $C_8$-aromatic hydrocarbon mixture so obtained is usually 0.05 to 3% by weight, typically 0.1 to 2% by weight. The non-aromatic hydrocarbon usually consist of 70 to 80% by weight of $C_8$-C paraffins and 20 to 30% by weight of $C_8$–$C_{10}$ naphthenes.

If the $C_8$-aromatic hydrocarbon mixture produced as above without going through the solvent extraction step can be directly used as a material in the xylene isomerization reaction, the cost of the material can be reduced, and the p-xylene manufacturers can offer p-xylene at a decreased price.

When the $C_8$-aromatic hydrocarbon mixture containing a small amount of non-aromatic hydrocarbons is continuously used as a starting material for p-xylene production by isomerization of xylenes, the non-aromatic hydrocrbons gradually build up in the process because of the reduced ability of the catalyst to convert the non-aromatic hydrocarbons, and adversely affect the xylene isomerization reaction itself. For example, if the reaction conditions are rendered severe to elevate the above converging ability, the yield of xylene will be decreased and finally, it becomes necessary to purge the the accumulated non-aromatic hydrocarbons out of the process.

Thus, although various processes have been proposed to date for the production of a $C_8$-aromatic hydrocarbon mixture having a relatively low content of non-aromatic hydrocarbons, an industrial process for producing p-xylene using such a $C_8$-aromatic hydrocarbon mixture as a material has not yet been perfected.

Recently, some literature references disclosing the intention of using the above raw material have been published. Examples are U.S. Pats. Nos. 4163028, 4312790, 4385195 and 4224141 and European Patent No. 102716 of Mobile Oil Corporation, U.S.A. Since in any of the methods disclosed in these references, the $C_8$-aromatic hydrocarbon mixture containing non-aromatic hydrocarbons is fed under very severe conditions (for example, at 427° C. and 230 psig) onto zeolite whose acid activity is reduced, side-reactions (such as disproportion and ring-cleavage reaction) consequently occur, and a decrease in the yield of xylene is noted. Furthermore in the continuous feeding of the hydrocarbon stock under severe conditions, the activity of the catalyst decreases with time, and the activity of converting the non-aromatic hydrocarbons is also reduced. As a result, these components build up in the recycling system, and are likely to reduce the efficiency of p-xylene production.

SUMMARY OF THE INVENTION

It is a primary object of this invention to provide a catalyst composition for advantageously isomerizing $C_8$-aromatic hydrocarbons mixture containing a small proportion of non-aromatic hydrocarbon which is relatively low in cost.

Another object of this invention is to provide a catalyst composition having excellent activity of decomposing non-aromatic hydrocarbons.

Another object of this invention is to provide a catalyst composition having high activity of isomerizing $C_8$-aromatic hydrocarbons, especially xylenes.

Another object of the invention is to provide a catalyst composition having high activity of isomerizing xylenes with a very little loss of xylenes by transalkylation, disproportionation reaction and benzene-ring hydrogenation reaction of $C_8$-aromatic hydrocarbons.

Another object of this invention is to provide a catalyst composition having high activity of decomposing non-aromatic hydrocarbons and isomerizing xylenes under relatively mild conditions.

Another object of this invention is to provide an industrially advantageous catalyst composition retaining stable catalytic activity for a long period of time.

Another object of the invention is to provide an advantageous process for decomposing non-aromatic hydrocarbons.

Another object of this invention is to provide a process for isomerizing a hydrocarbon feed stock composed of non-aromatic hydrocarbons and $C_8$-aromatic hydrocarbons.

Another object of this invention is to provide an industrial process for producing p-xylene from a hydrocarbon feed stock composed of non-aromatic hydrocarbons and $C_8$-aromatic hydrocarbons.

Further objects of this invention will become apparent from the following description.

The investigations of the present inventor have shown that the above objects of the invention along with its advantages are achieved by a catalyst composition consisting essentially of (a) a crystalline aluminosilicate zeolite having a silica/alumina mole ratio of at least 10, in which at least 50% of its cation sites are occupied by alkaline earth metal cations (component A), (b) a refractory inorganic oxide having platinum and tin supported thereon (component B), and (c) indium (component C), indium as component C being supported on the zeolite in component A and/or the refractory oxide in component B.

The present invention also provides a process for thermally decomposing non-aromatic hydrocarbons by using a catalyst comprising the above catalyts composition as an active ingredient, and also a process for vapor-phase isomerization of a hydrocarbon feed stock composed of non-aromatic hydrocarbons and $C_8$-aromatic hydrocarbons.

DETAILED DESCRIPTION OF THE INVENTION

The catalyst composition of this invention and its use will be described in detail.

Catalyst Composition

The catalyst composition of this invention consists essentially of the following components A, B and C:

(a) a crystalline aluminosilicate zeolite having a silica/alumina mole ratio of at least 10, in which at least 50% of its cation sites are occupied by alkaline earth metal cations (component A), (b) a refractory inorganic oxide having platinum and tin supported thereon (component B), and (c) indium (component C).

Indium as component C in the catalyst composion of this invention is supported on the zeolite in component A, and/or the refractory inorganic oxide in component B. Thus, the catalyst composition of this invention can be classified as any one of the following composition (i) to (iii).

(i) A catalyst composition consisting essentially of component A and component B having indium supported thereon.

(ii) A catalyst composition consisting essentially of component A having indium supported thereon and component B.

(iii) A catalyst composition consisting essentially of component A having indium supported thereon and component B having indium supported thereon.

The catalyst composition of this invention can be produced by uniformly mixing a powder of component A with or without indium (component C) supported thereon and a powder of component B with or without indium supported thereon, and then compression-molding the mixture into various shapes such as pellets and tablets.

The zeolite constituting component A in the catalyst composition is a crystalline aluminosilicate zeolite (to be referred to simply as "zeolite") having a silica/alumina mole ratio of at least 10. The silica/alumina mole ratio of the zeolite is preferably 20 to 2000, especially preferably 30 to 200.

The above zeolite is generally called "high silica zeolite", and well known as a catalyst base. Various ZSM-series zeolites developed by Mobil Oil Corporation are preferably used as the zeolite in component A of the catalyst compositon of this invention. Examples of he ZSM-series zeolites are ZSM-5 (see U.S. Pat. No. 3,702,886), ZSM-11 (see U.S. Pat. No. 3,709,979), ZSM-12 (see U.S. Pat. No. 3,832,449), ZSM-35 (see U.S. Pat. No. 4,016,245) and ZSM-38 (see U.S. Pat. No. 4,046,859).

Of these, zeolite ZSM-5 and zeolite ZSM-11 are preferred, and zeolite ZSM-5 is especially preferred.

It is critical that at least 50% of the cation sites [acid active sites based on alumina ($AlO_2^-$) as a constituent component of zeolite] should be occupied by alkaline earth metal cations. The use of zeolite in which at least 50% of its cation sites have been ion-exchanged with alkaline earth metal cations enables xylenes to reach the thermodynamically equilibrium composition and non-aromatic hydrocarbons to be decomposed selectively at high conversions while inhibiting a loss of xylenes in the hydrocarbon feed stock owing to the disproportionation of the xylenes.

Advantageously, at least 60%, preferably at least 65%, especially preferably 70 to 90%, of the cation sites of zeolite in component A are occupied by alkaline earth metal cations. The preferred range depends also upon the type of the alkaline earth metal cations. Generally, the ratio of exchange by the alkaline earh metal cations is preferably as high as possible. The upper limit of the exchange ratio, which depends upon the type of the metal cations, is usually in the range of about 70 to 90%. It is generally difficult to obtain zeolites ion-exchanged with higher proportions of alkaline earth metal cations than the above-indicated upper limit.

Examples of the alkaline earth metals to be ion-exchanged with the cation sites of the zeolite in component A are beryllium, magnesium, calcium, strontium and barium. Calcium and strontium are preferred, strontium being most suitable. Only one type of alkaline earth metal ions may be present in the cation sites of the zeolite, or ions of two or more kinds of alkaline earh metals may be present together. The present inventor presumed that these alkaline earth metal cations occupy the cation sites of the zeolite, and serve to reduce the acid activity of the zeolite and strengthen the steric restrictions of zeolite channels and consequently contribute greatly to inhibit the disproportionation reaction or transalkylation reaction of xylenes in the hydrocarbon feed stock.

Other cation sites of the zeolite in component A which are unoccupied by the alkaline earth cations are usually occupied by protonic or ammonium ion, and may be occupied by cations of metals such as alkali metals, iron, cobalt, nickel, copper, zinc, lanthanum and cerium.

Zeolites ion-exchanged with metal cations as well as alkaline earth metal cations may be obtained by known ion exchanging methods [see, for example, Journal of Catalysis, 46, 100-108 (1977) and Journal of Catalysis, 43, 292-303 (1976)].

Examples of alkaline earth metal compounds used to ion-exchange the cation sites of the zeolite with alkaline earth metal cations are nitrates such as calcium nitrate and strontium nitrate, chlorides such as calcium chloride and strontium chloride, and sulfates such as calcium sulfate and strontium sulfate. The refractory inorganic oxide (to be sometimes referred to as the "carrier") in component B may be any of those which are usually employed as a carrier for solid catalysts. Examples include alumina, silica, silica-alumina, kaolin, silica-magnesia, zirconia and magnesia. Alumina is suitable, and gamma-alumina is most suitable in view of its specific surface area.

The amount of platinum deposited on the carrier is generally 0.01 to 2.0% by weight, preferably 0.05 to 1.5% by weight, especially preferably 0.1 to 1.0% by weight, in order to inhibit the benzene-ring hydrogenation and decomposition of xylenes in the hydrocarbon feed stock as much as possible and promote the conversion of the non-aromatic hydrocarbons in the feed stock into lower boiling components. Platinum supported on the refractory inorganic oxide presumably functions to impart a marked action of converting the non-aromatic hydrocarbons owing to a synergistic effect produced by a combination of it with the zeolite described above. Platinum on the carrier also functions to impart the ability to selectively convert ethylbenzene contained in the hydrocarbon feed stock into benzene and ethane by de-ethylation rather than by disproportionation.

In addition to platinum, tin is deposited on the carrier in component B of the catalyst composiion of this invention. The function of tin on the carrier is considered to inhibit moderately the hydrogen dissociation adsorbing ability of platinum coexisting on the carrier and consequently, reduce markedly the benzene-ring hydrogenation and decomposition of the xylenes in the hydrocarbon feed stock while allowing the reacion of converting the non-aromatic hydrocarbons sufficiently into lower boiling components. From this viewpoint, the amount of tin deposited on the carrier is advantageously from 0.1//1 to 10/1, preferably from 0.3/1 to 7/1, especially 0.5/1 to 5/1, in terms of the atomic ratio of tin/platinum.

Desirably, platinum and tin in component B are dispersed highly and uniformly on the refractory inorganic oxide (carrier). By so doing, the activity of the catalyst compositon to decompose the non-aromatic hydrocaronbs in the hydrocarbon feed stock into lower boiling components becomes very stable with time.

In addition to platinum and tin, hydrochloric acid may also be supported on the carrier. Hydrochloric acid functions to disperse platinum and tin highly on the carrier. The amounnt of hydrochloric acid deposited on the carrier is generally 0.1 to 20 millimoles, preferably 0.5 to 10 millimoles, especially preferably 1 to 5 millimoles, based on the weight of the carrier.

The above-mentioned amount of hydrochloric acid is that actually used for deposition. The amount of hydrochloric acid actually supported on the carrier is considered to decrease from the above amount because of calcination during the preparation and use of the catalyst composition of this invention.

In preparing component B, the above components to be supported may be deposited successively in any desired sequence, or all at a time. Since the use of a platinum-tin-hydrochloric acid complex serves to disperse the above components uniformly on the surface of the carrier, it is especially preferable to employ a simultaneous depositing method which comprises preparing a uniform solution containing a platinum compound, a tin compound and hydrochloric acid, impregnating the refractory inorganic oxide with the resulting solution, removing the solvent, and then drying the resulting product.

Examples of platinum compounds used in preparing component B are chloroplatinic acid and a platinum-tetramine complex. Examples of the tin compound are soluble salts such as stannous chloride, tin sulfate and tetralkyl ammonium chlorostannate. Water, methanol, acetone, etc. may preferably be used as a solvent for dissolving these compounds.

The catalyst composition of this invention contains indium (component C) in addition to components A and B described above. Indium as component C exists deposited on the zeolite in component A and/or the refractory inorganic oxide in component B.

The function of indium in the catalyst composition of this invention is to further inhibit the ability of platinum to hydrogenate the benzene-ring of alkylated aromatic hydrocarbons which is inhibited by tin, and on the other hand, promote the reaction of converting non-aromatic hydrocarbons into lower boiling components. Furthermore, indium diffuses in the zeolite channels in component A and poisons its acid sites or strengthens the steric restricting effect in the channels; consequenly, indium reduces the disproportionation reacion or transalkylation reaction of $C_8$-aromatic hydrocarbons. It is not certain why indium produces this effect. But by bringing the catalyst composition of this invention containing indium into contact with the hydrocarbon feed stock, good xylene yields and high activity of converting the non-aromatic hydrocarbons into lower boiling components can be realized in comparison with the case of not adding indium.

The amount of indium (component C) in the catalyst composition is advantageously 0.01 to 10% by weight, preferably 0.1 to 5% by weight, based on the total amount of the zeolite in component A and the refractory inorganic oxide in component B. The amount of indium is that of metallic indium.

Advantageously, the atomic ratio of indium/platinum is generally from 0.1/1 to 10/1, preferably from 0.3/1 to 7/1, more preferably from 0.5/1 to 5/1.

The catalyst composition of this invention can be prepared by various methods. Generally, as described aboved, components A and B are first prepared separately, and then indium (component C) is deposited on one or both of components A and B. Finally, the resulting components A and B are mixed in suitable proportions. Alternatively, indium is deposited on at least one of components A and B during the preparation of components A and/or component B, and the resulting components are mixed.

Some typical methods of preparing the catalyst composition of this invention will be specifically described.

A first method comprises immersing component A in a solution of an indium compound, evaporating the solvent, drying component A, and then mixing component A with component B.

A second method involves depositing indium on component B. Preferably, it comprises immersing the refractory inorganic oxide optionally in the presence of hydrochloric acid in a uniform solution containing a platinum compound, a tin compound and an indium compound, evaporating the solvent, drying the refractory inorganic oxide, and then mixing the resulting product with component A.

A third method comprises immersing both components A and B in a solution of an indium compound, evaporating the solvent, and drying the resulting product. This method can be performed by sufficiently uniformly mixing both components A and B, immersing the mixture in a solution containing an indium compound or adding components in any desired order to the solution containing an indium compound, thus immersing components A and B in the solution, evaporating the solvent, and then drying the product, and then mixing the two components.

Examples of the indium compound used in each of the above methods include indium nitrate [$In(NO_3)_3.3H_2O$], indium sulfate [$In_{22}SO_4)_3.9H_2O$], indium trichloride ($InCl_3$), ammonium hexafluoroindate [$(NH_4)_3(InF_6$] and ammonium aquapentachloroindate [$(NH_4)_2$ ($InCl_5—H_2O$)].

The suitable ratio of the zeolite to the refractory inorganic oxide in the catalyst composition of this invention is from 10:90 to 90:10 by weight, preferably from 20:80 to 80:20, by weight.

The catalyst composition obtained as above is compressed into pellets, tablets or other shapes according to the purpose for which it is used.

Prior to use, the resulting catalyst composition is calcined in a stream of a gas containing at least 5% of oxygen at a temperature of 200° to 600° C., preferably 250° to 550° C., and then treated in a reducing atmosphere such as a hydrogen gas at 200° to 600° C., preferably 250° to 550° C. This reduction treatment is carried out usually after the calcined product is filled in a reactor.

It is assumed that in the resulting catalyst composition in use, platinum and tin in component B exist mostly as metals, and indium as component C exists in the form of a metal and/or an oxide.

The catalyst composition of this invention has high activity of decomposing non-aromatic hydrocarbons such as paraffins or naphthenes, and converting them into smaller molecules. According, the catalyst composition of this invention is used advantageously for decomposing or cracking a starting mixture containing non-aromatic hydrocarbons.

The catalyst of this invention has high activity of isomerizing $C_8$-aromatic hydrocarbons, particularly xylenes, very low activity of catalyzing disproportionation reaction or transalkylation reaction of xylenes and also of hydrogenating the benzene-ring of xylenes. It also has excellent activiy of de-ethylating ethylbenzene. Accordingly, when the catalyst composition of this invention is contacted with a hydrocarbon feed stock containing non-aromatic hydrocarbons and composed substantially of $C_8$-aromatic hydrocarbons whose thermodynamic equilibrium composition has not yet been reached, a high p-xylene approach to the thermodynamic equilibrium concentration is achieved with a very small loss of xylenes and a high decomposition ratio of non-aromatic hydrocarbons is obtained. Thus, the catalyst composition of this invention is suitable for an industrial process for isomerizing xylenes using $C_8$-aromatic hydrocarbons containing relatively inexpensive non-aromatic hydrocarbons.

Process for Decompositing Non-aromatic Hydrocarbons

The catalyst composition of this invention is used to decompose paraffins and/or naphthenes to obtain paraffins and/or naphthenes with a smaller number of carbon atoms. Generally, by contacting a starting mixture containing at least 50% by weight, preferably at least 60% by weight, of non-aromatic hydrocarbons containing at least 70% by weight, preferably at least 80% by weight, of $C_8$–$C_{14}$ paraffins and/or napthenes is contacted in the vapor phase in the presence of hydrogen with the catalyst composition. As a result, the paraffins and/or naphthenes are decomposed at high conversions to hydrocarbons having less than 8, particularly less than 7, carbon atoms.

The reaction temperature at this time is about 250° to about 450° C., preferably about 300° to about 430° C., especially preferably about 350° to about 410° C.

The reaction pressure is generally 0 to 25 kg/cm$^2$-G, preferably 0 to 20 kg/cm$^2$-G. Advantageously, the starting hydrocarbon mixture is fed at a weight hourly space velocity (hr$^{-1}$) of 0.5 to 100, preferably 2 to 50, especially preferably 5 to 20, per unit weight of the catalyst composition.

Hydrogen is fed into the hydrocarbon material at a hydrogen/hydrocarbon mole ratio of from 0.1 to 10, preferably from 0.5 to 5.

Process for Isomerizing $C_8$-Aromatic Hydrocarbons

According to the process of this invention, by contacting a hydrocarbon feed stock containing xylene isomers and non-aromatic hydrocarbons, the xylenes not reaching the thermodynamic equilibrium composition, with the catalyst composition at an elevated temperature in the vapor phase in the presence of hydrogen, the xylenes in the hydrocarbon feed stock can be allowed to reach the thermodynamic equilibrium concentration, and at the same time, the non-aromatic hydrocarbons are decomposed to lower boiling hydrocarbons.

The greatest feature of this invention is that a hydrocarbon feed stock which is composed mainly of $C_8$-aromatic hydrocarbons still containing non-aromatic hydrocarbons and which is relatively inexpensive can be used as a starting material, The hydrocarbon feed stock which can be used in the process of this invention is composed mainly of a $C_8$-aromatic hydrocarbon mixture and containing 0.02 to 5% by weight, preferably 0.05 to 3% by weight, especially preferably 0.1 to 3% by weight, based on the weight of the hydrocarbon feed stock, of non-aromatic hydrocarbons.

The composition of the hydrocarbon feed stock depending upon the composition of the starting raw material or the method of production, and cannot be strictly determined. The non-aromatic hydrocarbons are usually paraffines and naphthenes having 8 to 10 carbon atoms with a boiling point in the range of 120° to 150° C.

The non-aromatic hydrocarbons generally contain at least 70% by weight, particularly at least 80% by weight, of $C_9$–$C_{10}$ paraffins and naphthenes.

Typical components of the non-aromatic hydrocarbons include, for example, straight-chain paraffins such as octane, nonane and decane; monoalkylparaffines such as methylheptane, methyloctane, methylnonane, ethylhexane, ethylheptane and ehyloctane; dialkylparaffins such as dimethylhexane, dimethylheptane, dimethyloctane, methylethylpentane, methylethylhexane and methylethylheptane; trialkylparaffins such as trimethylhexane, trimethylheptane and dimethylethylpentane; and naphthenes such as trimethylcyclcohexanes and ethylmethylcyclohexanes.

By contact with the catalyst composition of this invention, the non-aromatic hydrocarbons are converted at high conversions into paraffins and naphthenes having less than 8, particularly less than 7, carbon atoms and can be easily separated by distillation.

The aromatic hydrocarbons in the hydrocarbon feed stock consists substantially of the $C_8$-aromatic hydrocarbon mixture. The $C_8$-aromatic hydrocarbon mixture may contain up to 40% by weight, particularly up to 20% by weight, based on the weight of the hydrocarbon feed mixture, of ethylbenzene in addition to the xylene isomers. Rarely, this hydrocarbon feed stock contains a tiny amount, usually not more than 0.5% by weight, based on the weight of the hydrocarbon feed stock, of $C_9$ aromatic hydrocarbons such as cumene, ethyltoluenes and trimethylbenzenes, but the presence of such tiny amounts of $C_9$-aromatic hydrocarbons does not affect the performance of the process of this invention. Thus, a hydrocarbon mixture containing such amounts of $C_9$-aromatic hydrocarbons may also be used as the hydrocarbon feed stock.

The hydrocarbon feed stock used in this invention for the isomerization of $C_8$aromatic hydrocarbons mainly contains xylene isomers which have not reached the thermodynamic equilibrium composition.

As is well known, xylene contains three isomers, ortho-, meta- and paraisomers. It is known that when a mixture in an arbitrary ratio of the three isomers is subjected to an isomerization reaction, the reaction reaches an equilibrium when the ratio among the three isomers attains a certain specific value, and apparently no further advance of the isomerization is noted. The composition of the xylene isomers in such an equilibrium state is called the "thermodynamic equilibrium composition". The thermodynamic equilibrium composition varies slightly depending upon temperature, and for example, the xylene isomers have the following thermodynamic equilibrium composition at the following temperature.

(1) Mixture consisting only of three xylene isomers (at 427° C.):

| | |
|---|---|
| p-Xylene | 23.4% by weight |
| m-Xylene | 52.1% by weight |
| o-Xylene | 24.5% by weight |

(2) Mixture of xylene isomers and ethylbenzene (at 427° C.):

| | |
|---|---|
| Ethylbenzene | 8.3% by weight |
| p-Xylene | 21.5% by weight |
| m-Xylene | 47.8% by weight |
| o-Xylene | 22.4% by weight |
| | 100% by weight in total |

In the present specification and the appended claims, the term "$C_8$-aromatic hydrocarbons not attaining the thermodynamic equilibrium composition" denotes a xylene isomer mixture in which the concentration of at least one of the three xylens isomers falls outside the thermodynamic equilibrium composition.

The reaction conditions used in the isomerization reaction of this invention, such as the temperature, pressure, WHSV (weight hourly space velocity; the velocity of feeding the starting material per unit weight of the catalyst per hour) and the hydrogen/hydrocarbon feed mole ratio, are selected from such ranges that bring the the xylene isomeric mixture in the hydrocarbon feed stock to the thermodynamic equilibrium composition and sufficiently decompose the non-aromatic hydrocarbons.

The reaction temperature may generally be within the range of 250° to 450 C., preferably 300° to 430° C., especially preferably 350° to 410° C. The choice of the reaction temperature is usually dominated by the concentration of the non-aromatic hydrocarbons contained in the hydrocarbon feed stock. It should be noted however that since the catalyst composition used in this invention has very high decomposing activity on the non-aromatic hydrocarbon components, the isomerization in 16ccordance with the process of this invention can be carried out under milder conditions than known processes. This greatly contributes to the stability of the catalyst composition with time.

Advantageously, the feed rate (WHSV) of the hydrocarbon feed stock per unit weight of the catalyst per hour in the process of this invention is generally 0.5 to 100, preferably 2 to 50, especially preferably 5 to 20. The reaction pressure may be selected freely within the range of generally 0 to 25 kg/cm$^2$-G, preferably 0 to 20 kg/cm$^2$-G. The purpose of the isomerization reaction is to allow the isomerization reaction of xylenes to proceed sufficiently, and simultaneously to decompose the non-aromatic hydrocarbons to lower boiling components and de-ethylate ethylbenzene contained in the feed stock.

For this purpose, the process of this invention is carried out in the presence of hydrogen. The proportion of hydrogen fed at this time is generally from 0.1 to 10, preferably from 0.5 to 5, in terms of the hydrogen/hydrocarbon mole ratio.

The present invention described above brings about the following excellent technical advantages over similar conventional techniques.

(1) An aromatic hydrocarbon mixture being relatively inexpensive and containing small amounts of non-aromatic hydrocarbons, which is produced by distillation alone without going through the step of removing non-aromatic hydrocarbons by solvent extraction, can be used as a starting material for isomerization of xylenes.

(2) Since the reaction conditions in isomerization are mild, coke formation on the catalyst can be inhibited. Even when the process is performed continuously over a long period of time, non-aromatic hydrocarbons do not build up in the xylene isomerization system, and the efficiency of xylene production facilities can be greatly increased.

(3) Since the hydrogenation reaction of the aromatic ring and the disproportionation reaction of xylenes can be markedly inhibited, the loss of xylenes is very little, and the isomerization yield or xylens increases.

(4) Since ethylbenzene contained in the feed stock can be de-ethylated highly selectively, the isomerization yield of xylenes increases, and conversion of by-products into lower boiling components is of additional value.

(5) The invention provides the catalyst composition having excellent activity not only on the isomerization of xylenes but also on the decomposition of non-aromatic hydrocarbons.

The following examples illustrate the present invention more specifically.

REFERENTIAL EXAMPLE 1

Preparation of $NH_4$-ZSM-5:

Zeolite ZSM-5 was synthesized by the method disclosed in Example 1 of U.S. Pat. No. 3,965,207.

Specifically, water glass was used as a source of silica; aluminum sulfate, as a source of alumina; and tri-n-propylamine and n-propyl bromide, as a source of an organic nitrogen cation. Methyl ethyl ketone was further added, and the above materials were reacted in an autoclave under predetermined conditions. The product was filtered, sufficiently washed with water, and dried overnight at 100° C. n an electric dryer. X-ray diffractometry identified the product as ZSM-5. As a result of chemical analysis, the product was found to have a silica/alumina mole ratio of 70.

The product was then treated with 10 ml, per gram of zeolite, of a 10% aqueous solution of ammoniunm chloride under reflux for 16 hours. This operation was repeated twice. The resulting product was separated by filtration, washed with water, and dried at 100° C. for 16 hours to give $NH_4^+$-type ZSM-5.

REFERENTIAL EXAMPLE 2

Preparation of Catalyst Components

A. Preparation of $Sr^{2+}$-ZSM-5

Ten grams of $NH_4^{30}$-ZSM-5 obtained in Referential Example 1 was treated with 100 ml of a 10% aqueous solution of strontium nitrate under reflux for 16 hours. This operation was repeated three times while replacing the aqueous strontium nitrate solution. The product was then separated by filtration, washed with water, and dried for 16 hours in an electric dryer at 100° C. to give $Sr^{2+}$-ZSM-5. Chemical analysis showed the product to contain 1.40% by weight of $Sr^{2+}$. This content corresponds to an $Sr^{2+}$exchange ratio of 73%.

A'. Preparation of $Ca^{2+}$-ZSM-5

$Ca^{2+}$-ZSM-5 was obtained in the same way as in A. except that calsium nitrate in the same concentration was used instead of strontium nitrate. .Chemical anslysis showed this product to contain 0.61% by weight of $Ca^{2+}$ which corresponded to a Ca exchange ratio of 69%.

B. Preparation of In-($Sr^{2+}$-ZSM-5)

Indium nitrate trihydrate (18.7 mg) was precisely weighed into a 100 ml eggplant-shaped flask, and dissolved in 15 ml of water. $Sr^{2+}$-ZSM-5 (3.0 g) prepared in Referential Example 2-A was suspended in the aqueous solution, and with stirring, maintained in a hot water bath at 50° C. ior 5 hours.

Water was evaporated at 45° C. by means of an evaporator to deposit indium on $Sr^{2+}$-ZSM-5. The powder in the flask was taken out, and dried in an electric dryer at 100° C. for 16 hours. The amount of indium deposited on $SR^{2+}$-ZSM-5 was 0.2% by weight.

C. Preparation of Pt-$Al_2O_3$

One gram of commercial chloroplatinic acid ($H_2PtCl_6.6H_2O$; special reagent grade produced by Wako Pure Chemical Industries, Ltd.) was dissolved in 650 ml of water. A portion (1.36 ml) of this solution was taken into a 50 ml eggplant-shaped flask and diluted with 20 ml of water. Five grams of gamma-alumina gel (ACP-1, a product of Catalysts and Chemicals Co., Ltd.) was added, and with stirring, the mixture was maintained at 50° C. for 5 hours. Thereafter, water was evaporated by a rotary evaporator at 40° C. under reduced pressure. Subsequently, the residue was dried in an electric dryer at 100° C. for 16 hours to give alumina containing 0.2% by weight of platinum.

D. Pt-In-$Al_2O_3$

Indium nitrate trihydrate (31.2 mg) was precisely weighed into a 50 ml. eggplant-shaped flask, and dissolved in 20 ml of water. Then, 1.36 ml of the same aqueous chloroplatinic acid solution as shown in C was added, and 5 g of gamma-alumina gel was also added. With stirring, the mixture was maintained at 50° C. for 5 hours. Then, by the same procedure as in Referential Example 2, C, alumina containing 0.2% by weight of platinum and 0.2% by weight of indium was prepared.

E. Preparation of Pt-Sn-HCl-$Al_2O_3$ 40.4 mg of stannous chloride dihydrate (special reagent grade, produced by Wako Pure Chemical Industries, Ltd.) was precisely weighed into a 50 ml eggplant-shaped flask, and dissolved in 20 ml of hydrochloric acid (special reagent grade, produced by Wako Pure Chemical Industries, Ltd.) and 20 ml of water. Furthermore, 1.36 ml of the same aqueous chloroplatinic acid solution as shown in C above was added. With stirring, the mixture was maintained at 50° C. for 5 hours. Then, by the same procedure as in Referential Example 2, C, alumina containing 0.2% by weight of platinum, 0.4% by weight of tin and 4.8 mmoles/g-alumina of hydrochloric acid was prepared, F. Preparation of Pt-In-Sn-HCl-$Al_2O_3$ Indium nitrate trihydrate (31.2 mg) and 40.4 mg of stannous chloride dihydrate were precisely weighed in a 50 ml eggplant-shaped flask, and dissolved in 20 ml of hydrochloric acid and 20 ml of water. Furthermore, 1.36 ml of the same aqueous chloroplatinic acid solution as indicated in C above was added. With stirring, the mixture was maintained at 550° C. for 5 hours. Thereafter, by the same procedure as in Referential Example 2, C, alumina containing 0.2% each of platinum and indium, 0.4% of tin and 4.8 mmoles/g-alumina of hydrochloric acid was prepared.

F'. Preparation of Pt-In-Sn-HCl-$Al_2O_3$

By repeating the procedure of F except that the amounts of the reagents were decreased to half, alumina containing 0.1% by weight each of platinum and indium, 0.2% by weight of tin and 2.4 mmoles/g-alumina of hydrochloric acid was prepared.

G. Preparation of Pt-In-Sn-$Al_2O_3$

By repeating the procedure of F except that hydrochloric acid was not used, alumina containing 0.2% by weight each of platinum and indium and 0.4% by weight of tin was prepared.

EXAMPLE 1

$Sr^{2+}$-ZSM-5 and Pt-In-Sn-HCl-$Al_2O_3$ prepared in Referential Example, 2, A and F were taken in equal amounts and sufficiently mixed in a mortar, and the mixture was molded into a size of 10 to 20 mesh. The molded catalyst was calcined in an electrical muffle furnace in a stream of air at 450° C., for 8 hours. Three grams of the catalyst was taken and filled in a pressurized fixed bed reactor. While nitrogen was passed through the catalyst bed, the temperature was elevated to 400° C. Then, nitrogen was replaced by a hydrogen stream, and the catalyst bed was heated at 400° C. under atmospheric pressure for 2 hours to reduce platinum contained in the catalyst composition. Then, the temperature was lowered to 380° C., the present reaction temperature, and the pressure was set at 7.4 kg/cm$^2$-G. A hydrocarbon feed stock of the composition shown in Table 1 was fed onto the catalyst at a rate of 30.0 g/hr together with hydrogen in a hydrogen/hydrocarbon feed stock mole ratio of 2:1.

The composition of the product and the reaction results after 50 hours from the start of feeding the hydrocarbon feed stock are shown in Table 1.

EXAMPLE 2

In-($Sr^{2+}$-ZSM-5) and Pt-Sn-HCl-$Al_2O_3$ prepared in Referential Example 2, B and E, respectively were taken in equal amounts, and sufficiently mixed in a mortar. The mixture was molded into a size of 10 to 20 mesh. By the method described in Example 1, the catalyst composition was pre-treated, and the same hydrocarbon feed stock as used in Example 1 was subjected to isomerization reaction under the same conditions as in Example 1. The composition of the product and the reaction results after 50 hours from the start of feeding the stock are shown in Table 1.

COMPARATIVE EXAMPLES 1-3

A mixture of equal amounts of $Sr^{2+}$-ZSM-5 and Pt-In-$Al_2O_3$ prepared in Referential Examples 2, A and D, respectively (Comparative Example 1), a mixture of equal amounts of In-($Sr^{2+}$-ZSM-5) and Pt-$Al_2SO_3$ prepared in Referential Examples 2,. B and C respectively (Comparative Example 2), and a mixture of equal amounts of $Sr^{2+}$-ZSM-5 and Pt-Sn-HCl $Al_2O_3$ prepared in Referential Examples 2. A and E respectively (Comparative Example 3) were used, and the same isomerization reaction as in Example 1 was carried out.

The composition of the product and the reaction results after 50 hours from the start of feeding the stock are shown in Table 1.

TABLE 1

| Metal component deposited on zeolite (component A) Metal component deposited on alumina (component B) | Composition of the feed stock (wt. %) | Composition of the product (wt. %) | | | | |
|---|---|---|---|---|---|---|
| | | Example 1 $Sr^{2+}$ Pt-In-Sn-HCl | Example 2 In-$Sr^{2+}$ Pt-Sn-HCl | Comparative Example 1 $Sr^{2+}$ Pt-In | Comparative Example 2 In-$Sr^{2+}$ Pt | Comparative Example 3 $Sr^{2+}$ Pt-Sn-HCl |
| Composition | | | | | | |
| $C_8$ non-aromatics | 0.027 | 1.277 | 1.562 | 2.574 | 2.315 | 2.300 |
| $C_9$ naphthenes | 0.229 | 0.170 | 0.142 | 0.109 | 0.124 | 0.137 |
| $C_9$ paraffines | 0.993 | 0.546 | 0.457 | 0.330 | 0.347 | 0.405 |
| Benzene | 0.010 | 2.325 | 2.306 | 1.476 | 1.426 | 3.001 |
| Toluene | 1.394 | 1.583 | 1.539 | 1.581 | 1.491 | 1.780 |
| Ethylbenzene (EB) | 11.748 | 8.209 | 8.088 | 9.010 | 9.339 | 7.076 |
| p-xylene (PX) | 8.973 | 20.447 | 20.439 | 19.869 | 19.665 | 20.308 |
| m-xylene | 57.469 | 45.360 | 45.425 | 45.444 | 45.847 | 44.978 |
| O-xylene | 19.060 | 19.195 | 19.185 | 19.001 | 18.980 | 19.064 |
| ethyltoluenes | 0.027 | 0.184 | 0.160 | 0.143 | 0.126 | 0.188 |
| trimethylbenzenes | 0.070 | 0.178 | 0.187 | 0.178 | 0.091 | 0.291 |
| diethylbenzenes | — | 0.426 | 0.399 | 0.301 | 0.264 | 0.356 |
| ethylxylenes | — | 0.204 | 0.182 | 0.108 | 0.095 | 0.211 |
| durene + | | — | 0.001 | — | — | — |
| Reaction results (%) | | | | | | |
| $C_9$ naphthene decomposition ratio | | 25.8 | 38.0 | 52.4 | 45.9 | 40.2 |
| $C_9$ paraffin decomposition ratio | | 45.0 | 54.0 | 66.8 | 65.1 | 59.2 |

TABLE 1-continued

| Metal component deposited on zeolite (component A) / Metal component deposited on alumina (component B) | Composition of the feed stock (wt. %) | Composition of the product (wt. %) Example 1 Sr2+ Pt-In-Sn-HCl | Example 2 In-Sr2+ Pt-Sn-HCl | Comparative Example 1 Sr2+ Pt-In | Comparative Example 2 In-Sr2+ Pt | Comparative Example 3 Sr2+ Pt-Sn-HCl |
|---|---|---|---|---|---|---|
| PX approach to equilibrium | | 103.0 | 103.2 | 99.7 | 94.6 | 103.6 |
| EB decomposition ratio | | 30.1 | 31.1 | 23.2 | 20.5 | 39.8 |
| Xylene losse decomposition ratio | | 0.585 | 0.530 | 1.389 | 1.181 | 1.347 |
| De-ethylation ratio | | 72.5 | 75.6 | 75.7 | 75.9 | 81.3 |
| Aromatic ring hydrogenation ratio | | 0.000 | 0.145 | 1.205 | 0.999 | 0.531 |

$C_9$ naphthene decomposition ratio =

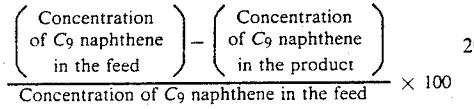

$$\frac{\left(\begin{array}{c}\text{Concentration}\\ \text{of } C_9 \text{ naphthene}\\ \text{in the feed}\end{array}\right)-\left(\begin{array}{c}\text{Concentration}\\ \text{of } C_9 \text{ naphthene}\\ \text{in the product}\end{array}\right)}{\text{Concentration of } C_9 \text{ naphthene in the feed}}\times 100$$

$C_9$ paraffin decomposition ratio =

$$\frac{\left(\begin{array}{c}\text{Concentration}\\ \text{of } C_9 \text{ paraffin}\\ \text{in the feed}\end{array}\right)-\left(\begin{array}{c}\text{Concentration}\\ \text{of } C_9 \text{ paraffin}\\ \text{in the product}\end{array}\right)}{\text{Concentration of } C_9 \text{ paraffin in the feed}}\times 100$$

$PX$ approach to equilibrium =

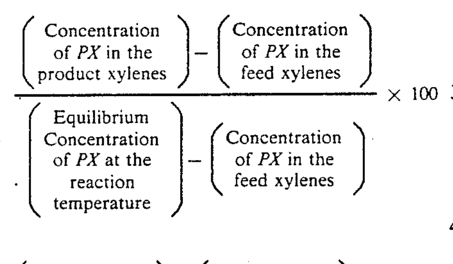

$$\frac{\left(\begin{array}{c}\text{Concentration}\\ \text{of } PX \text{ in the}\\ \text{product xylenes}\end{array}\right)-\left(\begin{array}{c}\text{Concentration}\\ \text{of } PX \text{ in the}\\ \text{feed xylenes}\end{array}\right)}{\left(\begin{array}{c}\text{Equilibrium}\\ \text{Concentration}\\ \text{of } PX \text{ at the}\\ \text{reaction}\\ \text{temperature}\end{array}\right)-\left(\begin{array}{c}\text{Concentration}\\ \text{of } PX \text{ in the}\\ \text{feed xylenes}\end{array}\right)}\times 100$$

$$\text{Xylene loss} = \frac{\left(\begin{array}{c}\text{Concentration}\\ \text{of xylenes}\\ \text{in the feed}\end{array}\right)-\left(\begin{array}{c}\text{Concentration}\\ \text{of xylenes}\\ \text{in the product}\end{array}\right)}{\text{Concentration of xylenes in the feed}}\times 100$$

De-ethylation ratio =

$$\frac{\left(\begin{array}{c}\text{Total moler of}\\ EB \text{ that}\\ \text{disappeared}\end{array}\right)-\left(\begin{array}{c}\text{Moler of } EB \text{ that}\\ \text{disproportionation}\\ \text{and trans-alkylation}\end{array}\right)}{\text{Total moler of } EB \text{ that disappeared}}\times 100$$

Aromatic ring hydrogenation ratio =

$$\frac{\left(\begin{array}{c}\text{Moler of the}\\ \text{benzene rings}\\ \text{in the feed}\end{array}\right)-\left(\begin{array}{c}\text{Moler of the}\\ \text{benzene rings}\\ \text{in the product}\end{array}\right)}{\text{Moler of the benzene rings in the feed}}\times 100$$

The results given in Table 1 show that in Comparative Examples 1 to 3, the loss of xylenes was very great because the ratio of hydrogenation of the aromatic ring was high, whereas in Examples 1 and 2, the loss of xylenes was drastically decreased, and the xylenes were isomerized to attain the thermodynamic equilibrium composition and simultaneously, the catalyst composition maintained high decomposing activity on naphthenes and paraffins.

EXAMPLE 3

With regard to the products of Example 1, the decomposition ratios of $C_9$ paraffins after the reaction were calculated, and are summarized in Table 2 (A).

TABLE 2 (A)

| $C_9$ paraffins | Decomposition ratio (%) |
|---|---|
| nonane | 66 |
| 2-methyl-octane | 52 |
| 3-methyl-octane | 44 |
| 4-methyl-octane | 41 |
| 3,4-dimethyl-heptane | 37 |
| 2,3-dimethyl-heptane | 31 |

The above table shows that the process of this invention can decompose bulky branched paraffins.

The proportions of the non-aromatic components contained in the feed stock and the product of Example 1 are shown in Table 2 (B).

TABLE 2 (B)

| Type | Feed stock (wt. %) | Product (wt. %) |
|---|---|---|
| C1 | 0 | 0 |
| C2 | 0 | 36.5* |
| C3 | 0 | 6.1 |
| C4 | 0 | 6.3 |
| C5 naphthene | 0 | 0.3 |
| C5 paraffin | 0.1 | 7.5 |
| C6 naphthene | 0 | 0.5 |
| C6 paraffin | 0.1 | 3.4 |
| C7 naphthene | 0 | 0.2 |
| C7 paraffin | 0.2 | 0.1 |
| C8 naphthene | 0.4 | 2.9 |
| C8 paraffin | 1.4 | 0.3 |
| C9 naphthene | 18.3 | 8.5 |
| C9 paraffin | 79.5 | 27.4 |

*The product of de-ethylation of ethylbenzene was included.

It is seen from Table 2 (B) that as a result of the reaction, $C_9$ naphthene and $C_9$ paraffins were mainly decomposed, and converted into $C_3$–$C_5$ *naphthenes and paraffins.*

EXAMPLE 4 AND COMPARATIVE EXAMPLE 4

In these examples, the effect of the content of $Sr^{2+}$ occupying the cation sites of the zeolite was examined. Specifically, by adjusting the concentration of the aqueous strontium nitrate solution used in Referential Example 2, A, Specifically, $Sr^{2+}$-ZSM-5 zeolites containing 0.68% by weight (Comparative Example 4) and 1.10% by weight (Example 4) of $Sr^{2+}$ were prepared. These zeolites weere mixed in equal amounts with Pt-In-Sn-HCl-$Al_2O_3$ prepared in Referential Example 2, F. By using these catalyst compositions, the same xylene isomerization reaction as in Example 1 was carried out.

The composition of the roduct and the reaction results afte 50 hours from the start of feding the feed stock are shown in Table 3.

It is seen from the data shown in Table 3 that in Example 4, the loss of xylenes was very low while maintaining high decomposition activity on non-aromatic hydrocarbons as compared with Comparative Example 4; and therefore that the process used in Example 4 is excellent for isomerization of xylenes.

TABLE 3

| | Composition of the feed stock (wt. %) | Composition of the product (wt. %) | |
|---|---|---|---|
| $Sr^{2+}$ content of zeolite | | 0.68 wt. % | 1.16 wt. % |
| $Sr^{2+}$ exchange rate | | 34% Comparative Example 4 | 58% Example 4 |
| **Composition** | | | |
| $C_8$ non-aromatics | 0.027 | 2.135 | 1.520 |
| $C_9$ naphthenes | 0.229 | 0.164 | 0.167 |
| $C_9$ paraffines | 0.993 | 0.495 | 0.510 |
| Benzene | 0.010 | 3.770 | 2.700 |
| Toluene | 1.394 | 2.012 | 1.696 |
| Ethylbenzene | 11.748 | 6.059 | 7.628 |
| p-Xylene | 8.973 | 20.307 | 20.306 |
| m-Xylene | 57.469 | 44.925 | 45.345 |
| O-Xylene | 19.060 | 19.027 | 19.140 |
| Ethyltoluenes | 0.027 | 0.174 | 0.196 |
| Trimethylbenzenes | 0.070 | 0.580 | 0.248 |
| Diethylbenzenes | — | 0.217 | 0.388 |
| Ethylxylenes | — | 0.228 | 0.235 |
| Durene+ | — | 0.004 | 0.001 |
| **Reaction results (%)** | | | |
| $C_9$ naphthene decomposition ratio | | 28.3 | 27.0 |
| $C_9$ paraffin decomposition ratio | | 50.0 | 48.6 |
| PX approach to equilibrium | | 103.8 | 102.6 |
| EB decomposition ratio | | 48.4 | 35.1 |
| Xylene losse decomposition ratio | | 1.454 | 0.832 |
| De-ethylation ratio | | 88.5 | 77.0 |
| Aromatic ring hydrogenation ratio | | 0.172 | 0.020 |

EXAMPLE 5

This examples is given to show that the catalyst of this invention gives very stable reaction results with time.

The composition of the product and the reaction results in Example 2 were analyzed also at the end of 12 hours, 84 hours, 124 hours, 204 hours and 252 hours after the feeding of the feed stock. Table 4 summarizes the reaction conditions and the results of analysis of the products. By comparing the reaction results at the end of 84 hours with those at the end of 204 hours, the catalyst of this invention was found to enable very stable production of p-xylene with time.

TABLE 4

| Reaction conditions | Composition of the feed stock (wt. %) | Composition of the product | | | | |
|---|---|---|---|---|---|---|
| Temperature (10° C.) | | 380 | 380 | 370 | 380 | 390 |
| WHSV ($hr^{-1}$) | | 10 | 10 | 10 | 10 | 10 |
| Total pressure ($kg/cm^2$-G) | | 7.5 | 7.4 | 7.4 | 7.4 | 7.4 |
| H2/Hc mole ratio | | 2.25 | 2.23 | 1.94 | 2.01 | 2.02 |
| Feed stock passing time (hours) | | 12 | 84 | 124 | 204 | 252 |
| **Composition** | | | | | | |
| $C_8$ non-aromatics | 0.027 | 1.657 | 1.512 | 1.090 | 1.382 | 1.831 |
| $C_9$ naphthenes | 0.229 | 0.138 | 0.148 | 0.161 | 0.148 | 0.128 |
| $C_9$ paraffines | 0.993 | 0.416 | 0.481 | 0.590 | 0.495 | 0.388 |
| Benzene | 0.010 | 2.321 | 2.230 | 1.668 | 2.238 | 2.900 |
| Toluene | 1.394 | 1.543 | 1.524 | 1.452 | 1.523 | 1.624 |
| Ethylbenzene | 11.748 | 8.077 | 8.258 | 9.002 | 8.186 | 7.315 |
| p-Xylene | 8.973 | 20.406 | 20.402 | 20.393 | 20.448 | 20.438 |
| m-Xylene | 57.469 | 45.414 | 45.441 | 45.733 | 45.506 | 45.242 |
| O-Xylene | 19.060 | 19.198 | 19.172 | 19.125 | 19.226 | 19.290 |
| Ethyltoluenes | 0.027 | 0.157 | 0.153 | 0.137 | 0.155 | 0.148 |
| Trimethylbenzenes | 0.070 | 0.192 | 0.172 | 0.123 | 0.174 | 0.241 |
| Diethylbenzenes | — | 0.383 | 0.397 | 0.413 | 0.400 | 0.353 |
| Ethylxylenes | — | 0.172 | 0.175 | 0.160 | 0.178 | 0.187 |
| Durene+ | — | 0.001 | — | — | — | — |
| **Reaction results (%)** | | | | | | |
| $C_9$ naphthene decomposition ratio | | 39.7 | 35.4 | 29.7 | 35.4 | 44.1 |
| $C_9$ paraffin decomposition ratio | | 58.1 | 51.6 | 40.6 | 50.2 | 60.9 |
| PX approach to equilibrium | | 103.1 | 103.0 | 102.2 | 103.1 | 103.8 |
| EB decomposition ratio | | 31.3 | 29.7 | 23.4 | 30.3 | 37.7 |
| Xylene losse decomposition ratio | | 0.566 | 0.570 | 0.293 | 0.376 | 0.622 |
| De-ethylation ratio | | 76.6 | 74.9 | 68.1 | 75.1 | 81.7 |
| Aromatic ring hydrogenation ratio | | 0.183 | 0.158 | 0.079 | 0.046 | 0.087 |

HC = Hydrocarbon

EXAMPLE 6

This example shows the effect of $Ca^{2+}$ as metal cations occupying the cation sites of zeolite. Specifically, $Ca^{2+}$-ZSM-5 and Pt-Sn-In-HCl-$Al_2O_3$ prepared in Referential Example 2, A' and F respectively, were mixed in equal amounts, and then, by the same procedure and reaction condtions as described in Example 1, isomerization reaction of xylenes was carried out. The composition of the product and the reaction results after 50 hours from the feeding of the feed stock are shown in Table 5.

The results given in Table 5 show that when $Ca^2$ occupied the cation sites of zeolite, too, the loss of xylenes decreased, the xylenes were sufficiently isomerized to such an extent that they attained the thermodynamic equilibrium composition, and at the same time, naphthenes and paraffines were decomposed.

TABLE 5

| | Composition of the feed stock (wt. %) | Composition of the product (wt. %) |
|---|---|---|
| Composition | | |
| $C_8$ non-aromatics | 0.018 | 1.347 |
| $C_9$ naphthenes | 0.216 | 0.172 |
| $C_9$ paraffines | 1.066 | 0.851 |
| Benzene | 0.026 | 2.828 |
| Toluene | 1.468 | 1.792 |
| Ethylbenzene | 11.809 | 7.325 |
| p-Xylene | 8.863 | 20.217 |
| m-Xylene | 57.099 | 44.918 |
| O-Xylene | 19.317 | 19.126 |
| Ethyltoluenes | 0.044 | 0.261 |
| Trimethylbenzenes | 0.013 | 0.253 |
| Diethylbenzenes | | 0.510 |
| Ethylxylenes | | 0.459 |
| Durene+ | | 0.020 |
| Reaction results (%) | | |
| $C_9$ naphthene decomposition ratio | | 20.4 |
| $C_9$ paraffin decomposition ratio | | 20.2 |
| PX approach to equilibrium | | 103.0 |
| EB decomposition ratio | | 38.0 |
| Xylene losse decomposition ratio | | 1.194 |
| De-ethylation ratio | | 69.6 |
| Aromatic ring hydrogenation ratio | | 0.186 |

EXAMPLE 7

This example shows the results obtained when the mixing ratio of the zeolite component to the alumina component was varied. Specifically, $Sr^{2+}$-ZSM-5 and Pt-Sn-In-HCl-$Al_2O_3$ obtained in Referential Example 2, A and F' respectively were mixed in a weight ratio of 1:2. The resulting catalyst (4.5 g) was filled in a pressurized solid bed reactor, and otherwise by the same procedure and under the same condition as in Example 1, isomerization of xylenes was carried out. The composition of the product and the results of the reaction after 50 hours from the feeding of the feed stock are shown in Table 6.

The results in Table 6 show that the loss of xylenes was drastically decreased, the xylenes were isomerized to attain the thermodynamic equilibrium concentration, and that at the same time, naphthenes and paraffins were decomposed with good efficiency.

TABLE 6

| | Composition of the feed stock (wt. %) | Composition of the product (wt. %) |
|---|---|---|
| Composition | | |
| $C_8$ non-aromatics | 0.118 | 1.489 |
| $C_9$ naphthenes | 0.222 | 0.156 |
| $C_9$ paraffines | 1.056 | 0.562 |
| Benzene | 0.002 | 2.347 |
| Toluene | 1.490 | 1.724 |
| Ethylbenzene | 11.848 | 8.128 |
| p-Xylene | 8.852 | 20.436 |
| m-Xylene | 57.191 | 45.261 |
| O-Xylene | 19.158 | 18.939 |
| Ethyltoluenes | 0.057 | 0.247 |
| Trimethylbenzenes | 0.007 | 0.123 |
| Diethylbenzenes | | 0.459 |
| Ethylxylenes | | 0.149 |
| Durene+ | | 0.149 |
| Reaction results (%) | | |
| $C_9$ naphthene decomposition ratio | | 28.8 |
| $C_9$ paraffin decomposition ratio | | 46.8 |
| PX approach to equilibrium | | 103.7 |
| EB decomposition ratio | | 31.4 |
| Xylene losse decomposition ratio | | 0.663 |
| De-ethylation ratio | | 72.8 |
| Aromatic ring hydrogenation ratio | | 0.076 |

EXAMPLE 8

This examples shows the effect of hydrochloric acid on the refractory inorganic oxide (component (B) having platinum and tin supported thereon in the catalyst composition.

$Sr^{2+}$-ZSM-5 and Pt-Sn-In-$Al_2O_3$ prepared in Referential Example 2, A and G respectively were mixed in equal amounts. By using the mixture, the isomerization of xylenes was carried out by the same procedure and under the same conditions as in Example 1. The composition of the product and the reaction results after 50 hours from the start of feeding the feed stock are shown in Table 7.

The results given in Table 7 show that when component B did not contain hydrochloric acid, the inhibition of xylene loss attributed to hydrogenation of the aromatic ring was slightly insufficient as compared with the results of Example 1, but the other results were satisfactory.

TABLE 7

| | Composition of the feed stock (wt. %) | Composition of the product (wt. %) |
|---|---|---|
| Composition | | |
| $C_8$ non-aromatics | 0.111 | 1.470 |
| $C_9$ naphthenes | 0.205 | 0.154 |
| $C_9$ paraffines | 0.993 | 0.585 |
| Benzene | 0.001 | 2.197 |
| Toluene | 1.472 | 1.685 |
| Ethylbenzene | 11.843 | 8.349 |
| p-Xylene | 8.859 | 20.276 |
| m-Xylene | 57.221 | 45.349 |
| O-Xylene | 19.248 | 19.072 |
| Ethyltoluenes | 0.040 | 0.221 |
| Trimethylbenzenes | 0.007 | 0.103 |
| Diethylbenzenes | | 0.437 |
| Ethylxylenes | | 0.142 |
| Durene+ | | |
| Reaction results (%) | | |
| $C_9$ naphthene decomposition ratio | | 24.8 |
| $C_9$ paraffin decomposition ratio | | 41.1 |
| PX approach to equilibrium | | 102.3 |
| EB decomposition ratio | | 29.5 |
| Xylene losse decomposition ratio | | 0.739 |
| De-ethylation ratio | | 72.4 |
| Aromatic ring hydrogenation ratio | | 0.192 |

We claim:

1. A catalyst composition consisting essentially of (a) a crystalline aluminosilicate zeolite having a silica/alumina mole ration of at least 10, in which at least 50% of its cation sites are occupied by alkaline earth metal cations (component A), (b) a refractory inorganic oxide having platinum and tin supported thereon (component B), and (c) indium (component C), indium as component C being supported on the zeolite in component A and/or the refractory oxide in component B.

2. The catalyst composition of claim 1 in which the silica/alumina mole ratio in the crystalline aluminosilicate zeolite is at least 30.

3. The catalyst composition of claim 1 in which the crystalline aluminosilicate zeolite is zeolite ZSM-5.

4. The catalyst composition of claim 1 in which the crystalline aluminosilicate zeolite is zeolite ZSM-11.

5. The catalyst composition of claim 1 in which the alkaline earth metal cations are strontium or calcium cations.

6. The catalyst compositon of claim 1 in which the alkaline earth metal cations are strontium cations.

7. The catalyst compositon of claim 1 in which at least 60% of the cation sites of the crystalline aluminosilicate zeolite are occupied by the alkaline earth metal cations.

8. The catalyst composition of claim 1 in which the refractory inorganic oxide is alumina.

9. The catalyst composition of claim 1 in which platinum is supported in an amount of 0.01 to 2% by weight based on the refractory inorganic oxide.

10. The catalyst composition of claim 1 in which tin is supported in an amount such that the tin/platinum atomic ratio is from 0.1:1 to 10:1.

11. The catalyst composition of claim 1 in which the amount of indium is 0.01 to 10% by weight based on the crystalline aluminosilicate zeolite and the refractory inorganic oxide combined.

12. The catalyst composition of claim 1 in which component B further comprises hydrochloric acid.

13. The catalyst composition of claim 12 in which the amount of hydrochloric acid is 0.2 to 20 millimoles per gram of the refractory inorganic oxide.

14. The catalyst composition of claim 1 in which the weight ratio of the crystalline aluminosilicate zeolite to the refractory inorganic oxide is from 10:90 to 90:10.

* * * * *